United States Patent [19]

Cohen et al.

[11] Patent Number: 5,739,170
[45] Date of Patent: Apr. 14, 1998

[54] INHIBITORS OF METAZOAN PARASITE PROTEASES

[75] Inventors: Fred E. Cohen; James H. McKerrow; George L. Kenyon, all of San Francisco, Calif.; Zhe Li, Malden, Mass.; Xiaowu Chen; Baoqing Gong, both of San Francisco, Calif.; Rongshi Li, San Diego, Calif.

[73] Assignee: The Regents of the University of California, Oakland, Calif.

[21] Appl. No.: 413,337

[22] Filed: Mar. 30, 1995

Related U.S. Application Data

[63] Continuation-in-part of Ser. No. 387,760, Mar. 28, 1995, Pat. No. 5,610,192, which is a continuation-in-part of Ser. No. 943,925, Sep. 11, 1992, abandoned.

[30] Foreign Application Priority Data

Sep. 11, 1993 [WO] WIPO .................. PCT/US93/08708

[51] Int. Cl.⁶ .................. A61K 31/12; A61K 31/135
[52] U.S. Cl. .................. 514/685; 514/646; 514/676
[58] Field of Search .................. 514/685, 646, 514/676

[56] References Cited

PUBLICATIONS

Chen et al., *Antimicrobial Agents and Chemotheraph*, "Licochalone A, a New Antimalarial Agent, Inhibits in Vitro Growth of the Human Malaria Parasite *Plasmidium falciparum* and Protects Mice from *P. yoelii* infection", 38:1470–75, 1994.

*Chemical Abstracts*, "Bioflavonoid effects on in vitro cultures of *Plasmodium falciparum*. Inhibition of permeation pathways induced in the host cell membrane by intraerythrocytic parasite", 110(11)18, column 2, abstract No. 87987p, Biochem. Parmacol., 37(22):4269–76, 1989.

Proceedings of the National Academy of Sciences, vol. 90, Issued Apr. 1993, Ring et al "Structural–Based Inhibitor Design by Using Protein Models for the Development of Antiparasitic Agents" pp. 3583–3587.

Chemical Abstracts, vol. 115, No. 14, Issued 1991, Rheinberger et al. "Incorporation of Fluorescent Substances into Dental Materials for Differentiation from Surrounding Tissue,"0 See Abstract No. 142380, Ger. Offen. DE 3939998.

Chemical Abstracts, vol. 81 No. 12, Issued 1974, Mucke, H., "Possibilities of Coloring Peracetic Acid for Skin Disinfection" See Abstract No. 68513, Pharmazie 29(3), 206–7.

Chemical Abstracts, vol. 113, No. 22, Issued 1989, Kino and Kato, "Hair Dye Taining Water–Soluble Dyes, Carbon Black, and Nonionic Surfactants," See Abstract No. 197653, JP 01242518.

Sweeney et al. "Burger's Medicinal Chemistry" Fourth Edition, Part II. Published 1981 by John Wiley & Sons (N.Y.) pp. 342–345).

Santi et al. "Burger's Medicinal Chemistry" Fourth Edition, Part II. Published 1981 by John Wiley & Sons (N.Y.) pp. 350–351.

Rosenthal et al. The American Society for Clinical Investigation, Inc. "Antimalarial Effectis of Peptide Inhibitors of *Plasmodium falciparum* Cysteine Proteinase" vol. 88, Nov. 1991, 1467–1472.

*Primary Examiner*—Phyllis G. Spivack
*Attorney, Agent, or Firm*—Townsend and Townsend and Crew LLP

[57] ABSTRACT

Compositions and methods are disclosed for treating a patient infected with a metazoan parasite by inhibiting the enzymatic action of the metazoan parasite protease, wherein there is employed at least one compound of formula I

A—X—B wherein A is a substituted or unsubstituted homoaromatic ring system comprising one to three rings which bind to at least one of the S2, S1 and S1' subsites; B is a substituted or unsubstituted homoaromatic ring system comprising one to three rings which bind to at least one of the S1', S1 and S2 subsites; and X is —C=C—C(=O)—. These compositions and methods have particular utility in the treatment of schistosomiasis, malaria, and other infectious diseases.

9 Claims, No Drawings

INHIBITORS OF METAZOAN PARASITE PROTEASES

This application is a continuation-in-part of U.S. application Ser. No. 08/387,760 filed Mar. 28, 1995 based on PCT International Application PCT US93/08708 filed Sep. 13, 1993 (corresponding to PCT published application WO 94/06280, published on Mar. 31, 1994), which in turn is a continuation-in-part of U.S. application Ser. No. 07/943,925 filed Sep. 11, 1992, now abandoned.

This invention was made with Government support under Contract No. MDA 972-91-J-1013, awarded by DARPA (now called ARPA), a division of the Department of Defense; and Grant No. 890499 awarded by UNDP/World Bank/WHO Special Programme for Research and Training in Tropical Diseases (TDR). The Government has certain rights in this invention.

BACKGROUND OF THE INVENTION

This invention relates generally to compositions and methods useful in the treatment of certain infectious diseases. More specifically, the invention relates to compositions which inhibit proteases, such as malaria cysteine protease. Compounds that inhibit these proteases are useful in the prevention and treatment of malaria, schistosomiasis and other infectious diseases.

Proteases are involved in many important biological processes including protein turnover, blood coagulation, complement activation, hormone processing, and cancer cell invasion. Thus, they are frequently chosen as targets for drug design and discovery. The critical role certain proteases play in the life cycle of parasitic organisms also makes them attractive drug design targets for certain infectious diseases.

Schistosomiasis (bilharziasis) is a parasitic disease caused by schistosomes (blood flukes) that generally live in the veins of the gut and liver of a human host. Adult worms can survive up to 20 years. Female adult worms release thousands of eggs each day, which often find their way to tissues such as liver, brain, and lung, where they cause considerable damage by stimulating the body to form inflammation and scar tissue around them. Most eggs pass through the bladder or wall of the gut. Once outside, they hatch and infect water snails. The parasite multiplies inside the snail, giving rise to thousands of cercariae that exit the snail and swim free in search of a host in which to complete their life cycle.

Malaria is another well known infectious disease caused by protozoa of the genus Plasmodium, which are transmitted by bites of infected mosquitoes. Infection with *Plasmodium falciparum*, the most virulent human malarial pathogen, is estimated to be responsible for over 1 million deaths each year. The most valuable of the heretofore developed classes of antimalarial drugs are the quinoline-containing compounds, such as chloroquine and mefloquine; chloroquine has been especially effective as both a preventative and a curative. A serious problem in the treatment and control of malaria has been the increasing resistance of populations of *P. falciparum* to these known antimalarial drugs. In addition, reports of multi-drug resistance makes the search for novel therapies especially urgent. Thus, there remains a great need to identify new compounds that have antimalarial capabilities.

During the trophozoite stage, the parasites infect red blood cells (erythrocytes) where they reproduce asexually. At the completion of each asexual cycle, the red blood cells lyse and merozoites are released which invade new red blood cells. This cycle of lysis and re-infection is responsible for the major clinical manifestations of malaria.

Most anti-malarials are blood schizontocides which are active against the parasites during the intra-erythrocytic stage of its life cycle. Sulphones and sulphonamides inhibit the synthesis of dihydrofolic acid, while biguanides and diaminopyrimidines inhibit the synthesis of tetrahydrofolic acid. Although the mechanism of these anti-malarials is known to involve interference with the parasites' ability to synthesize nucleic acids [Bruce-Chwatt, L. J., *Essential Malariology* (Wiley, New York (1985)], the mechanism of action of the quinoline-containing compounds has until recently been surprisingly elusive. Recent work provides evidence that the quinoline derivatives work by interfering with the detoxification activity of a heme polymerase [Slater and Cerami, *Nature* 355, 167 (1992)], although this has recently been called into question [Dorn et al., *Nature* 374, 269 (1995)].

During the erythrocytic phase, the parasites degrade hemoglobin as a primary source of amino acids. Rosenthal and co-workers have identified a critical cysteine protease involved in the degradation of hemoglobin, the parasites' primary source of amino acids [Rosenthal, P. J. et al., *J. Clin. Invest.* 82, 1560 (1988)]. Blocking this enzyme with cysteine protease inhibitors (such as E-64 and Z-Phe-Arg-FMK) in culture arrests further growth and development of the parasites [Rosenthal, P. J. et al., *Mol. Biochem. Parasitol.* 35, 177 (1989)]. Because humans (and, probably, most other mammals) do not have an analogous hemoglobinase, inhibition of this protease (either alone or in conjunction with established therapies) provides an attractive strategy for the treatment of malaria. Moreover, inhibition of analogous proteases present in other metazoan parasites would similarly provide potentially valuable techniques for treatment of human and animal patients infected with those parasites.

The aforementioned PCT published application WO 94/06280, the entire disclosure of which is hereby incorporated by reference, describes various classes of metazoan protease inhibitors containing specific structural elements which bind to the S2 subsite and at least one of the S1 and S1' subsites of the metazoan parasite protease. The protease inhibitors described therein generally include at least two homoaromatic or heteroaromatic ring systems, each comprising one to three rings, joined together by suitable linkers. The linkers concretely exemplified therein in every instance comprise at least two nitrogen atoms as a part of the backbone thereof.

It is an object of the present invention to provide compositions and methods for treatment of malaria and other infectious diseases caused by metazoan parasites.

SUMMARY OF THE INVENTION

In accordance with the present invention, there are provided compositions and methods for treating a patient infected with a metazoan parasite by inhibiting the enzymatic action of the metazoan parasite protease, wherein there is employed at least one compound of general formula I

wherein A is a substituted or unsubstituted homoaromatic or heteroaromatic ring system comprising one to three rings which binds to at least one of the S2, S1 and S1' subsites;

B is a substituted or unsubstituted homoaromatic or heteroaromatic ring system comprising one to three rings which binds to at least one of the S1', S1 and S2 subsites; and X is —C=C—C(=O)—.

These compositions and methods have particular utility in the treatment of schistosomiasis, malaria, and other infectious diseases. The compositions of the present invention are useful, for example, to inhibit the action of trophozoite cysteine protease, thereby preventing degradation of hemoglobin, the primary source of amino acids for the pathogen that causes human malaria. The methods of the present invention comprise administration to a patient infected with a metazoan parasite of at least one metazoan protease inhibitor of general formula I in an amount effective to inhibit the protease of the metazoan parasite, thereby killing the parasite.

DETAILED DESCRIPTION OF THE INVENTION

Pursuant to the present invention, compositions and methods for inhibiting the enzymatic action of metazoan parasite proteases comprising an effective amount of at least one metazoan protease inhibitor of general formula I are provided. These compositions have utility in the prevention and treatment of schistosomiasis, malaria, and other infectious diseases. In the case of malaria, the compositions of the invention inhibit the trophozoite cysteine protease. In schistosomiasis, the enzyme inhibited by the compositions of the invention is the adult cysteine protease (or "hemoglobinase").

The inhibitors of the present invention have particular utility against the metazoan parasites *Plasmodium falciparum* (which causes malaria), *Schistosoma mansoni* (which causes schistosomiasis), and *Trypanosoma cruzi* (which causes Chagas' disease). In addition, proteases specific to the following metazoan parasites may also be inhibited by compositions in accordance with the present invention: *Giardia lamblia, Entoemeba histolytica, Cryptospiridium spp., Leishmania spp., Brugia spp., Wuchereria spp., Onchocerca spp., Strongyloides spp., Coccidia, Haemanchus spp., Ostertagia spp., Trichomonas spp., Dirofilaria spp., Toxocara spp., Naegleria spp., Pneumocystis carinii, Ascaris spp.,* other *Trypanosoma spp.,* other *Schistosome spp.,* other *Plasmodium spp., Babesia spp., Theileria spp., Anisakis* and *Isospora beli*.

As described in the aforementioned PCT published application WO 94/06280, optimal ring systems and spacer lengths were determined for protease inhibitors which bind to the S2 and S1' subsites. In addition, compounds comprising aromatic ring systems characteristic of the inhibitors useful for binding to the S2 and S1' subsites but joined by shorter linkers than would be appropriate for bridging these subsites were also found to be effective in inhibiting metazoan parasite proteases. Modeling studies with these shorter compounds indicated that one of the aromatic ring systems binds to the S2 subsite and the second aromatic ring system of the shorter compounds binds to the S1 or S1' subsite (but cannot fill all three subsites fully). By introduction of a third aromatic ring system into the shorter inhibitors it was possible to construct compounds that fit fully all three pockets of the target site of the enzyme (the S2, S1 and S1' subsites).

Pursuant to the present invention, a broad class of metazoan parasite protease inhibitors have been identified as of particular utility in accordance with the present invention having the general formula

A—X—B wherein A is a substituted or unsubstituted homoaromatic or heteroaromatic ring system comprising one to three rings which binds to at least one of the S2, S1 and S1' subsites;

B is a substituted or unsubstituted homoaromatic or heteroaromatic ring system comprising one to three rings which binds to at least one of the S1', S1 and S2 subsites; and X is —C=C—C(=O)—.

Both homoaromatic ring systems and heteroaromatic ring systems bearing a substituent containing a heteroatom (O, N) and/or heterocyclic systems with charged atoms (in particular, quinoline) are contemplated as within the scope of the invention. In a preferred class of inhibitors in accordance with the present invention, B binds to the S1 subsite. In a preferred subclass of inhibitors, B has the structure -B'-X'-B", wherein B' is an aromatic ring system which binds to the S1 subsite, B" is an aromatic ring system which binds to the S1' subsite, and X' is a direct bond or a linker with a backbone of one to three atoms in length.

Each of the ring systems A and B is preferably a one- or two-ring homoaromatic (e.g., phenyl, 1-naphthyl, 2-naphthyl, etc.) or heteroaromatic group which has an affinity for the S2 or S1' and S1 subsites, respectively. The ring system A or B may be unsubstituted; preferably, however, the ring system bears at least one non-interfering substituent (as hereinafter defined) which does not interfere with, and may actually promote, binding via interactions with the side chains with hydrophobic features, side chains and polypeptide backbone elements with donor and acceptor sites for hydrogen bonds and side chains with formal charges for electrostatic interactions characteristic of the subsite to which it binds.

Particular examples of suitable ring systems include, but are not limited to, the following: phenyl; pyridyl; naphthyl; isoquinolyl; phthalazinyl; coumarinyl; phenanthryl; and quinolyl. Again, all of these ring systems may be unsubstituted or substituted by one or more non-interfering substituents as hereinafter defined. Preferred embodiments of A are phenyl, naphthyl, pyridyl and isoquinolyl; preferred embodiments of B are phenyl and pyridyl.

The choice of a particular structure for use as ring system B depends to some extent on whether the inhibitor is being designed for use to block the S1' and/or the S1 subsite. In general, it has been determined that for binding to the S1' subsite, a two-ring system (for example, as described for use as Group A) is more effective than a one-ring system. Multiple-ring systems (and in particular, two-ring systems) as previously described as useful in binding to the S2 and S1 subsites are also presently preferred for binding to the S1' subsite.

As previously noted, both the ring systems A and B and the linker X may suitably bear one or more non-interfering substituents. For purposes of the present invention, a non-interfering substituent is defined as one which does not interfere with bonding of the ring structures to the active site of the enzyme due to steric and/or electronic factors; in some cases, the presence of particular non-interfering substituents is believed to promote bonding by interaction of these substituents with structural elements of the enzyme in the proximity of the active site. In most instances, the primary consideration with respect to possible substituents is a steric one; for the most part, relatively bulky substituents are not particularly preferred for use in the inhibitors of the present invention. Suitable non-interfering substituents include, but are not limited to, the following: hydroxyl, including protected hydroxyl (i.e., a hydroxyl group which is protected by a suitable art-recognized protective group); lower alkyl; lower alkoxy; amino, mono- and di-(lower-alkyl)-amino; amino-, mono- and di-(lower-alkyl)-amino-lower-alkoxy; —COOH and —COOR', wherein R' is lower alkyl or aryl; —NO₂; halogen (in particular, Cl, F and Br); aryl (in particular, phenyl and benzyl); and aryloxy (in particular, phenoxy and benzyloxy). For purposes of the present invention, by lower alkyl is meant an alkyl group of one to five, and preferably one to three, carbon atoms.

Pursuant to one particular embodiment of the present invention, the inhibitors have the general formula II

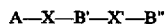

and are designed to bind fully to the S2, S1 and S1' subsites. In these structures, X' is exemplified as follows: a direct ring-to-ring bond; a single-atom backbone linker (e.g., —CH₂—); and a two-atom backbone linker (e.g., —CH₂—O— and —N=N—). Other X' linkers (e.g., those specified as suitable for use as X in the compounds of PCT published application WO 94/06280) would be readily apparent substitutes for these exemplary structures. It is presently preferred that A and B' are both phenyl, B" is 1-imidazolyl and X' is a direct bond. As indicated with respect to the previous structures, however, these examples should be viewed as merely illustrative of the range of structures which may be employed as ring system A, ring system B' and ring system B", and once again analogous ring systems and substitution patterns other than those depicted herein are clearly contemplated as within the scope of the present invention.

Particular inhibitors suitable for use in the compositions and methods of the present invention include a number of general classes of compounds which have been investigated in some detail. One such class of compounds has the general formula III

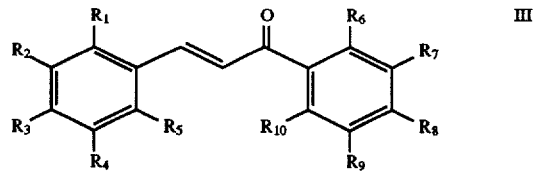

wherein $R_1$ is selected from the group consisting of hydrogen, $CF_3$, hydroxyl, lower alkyl, lower alkoxy and halogen; $R_2$ is selected from the group consisting of hydrogen, $CF_3$, hydroxyl, lower alkyl, lower alkoxy and halogen; $R_3$ is selected from the group consisting of hydrogen, $CF_3$, hydroxyl, lower alkyl, lower alkoxy, nitro, lower-alkylamino, di-lower-alkylamino and halogen; $R_4$ is selected from the group consisting of hydrogen, $CF_3$ and halogen; $R_5$ is selected from the group consisting of hydrogen, $CF_3$, lower alkyl, lower alkoxy and halogen; $R_6$ is selected from the group consisting of hydrogen, $CF_3$, hydroxyl, lower alkyl, lower alkoxy, lower-alkylamino-lower-alkoxy, di-lower-alkylamino-lower-alkoxy and halogen; $R_7$ is selected from the group consisting of hydrogen, $CF_3$, hydroxyl, lower alkyl, lower alkoxy, lower-alkylamino-lower-alkoxy, di-lower-alkylamino-lower-alkoxy and halogen; $R_8$ is selected from the group consisting of hydrogen, $CF_3$, hydroxyl, lower alkyl, lower alkoxy, lower-alkylamino-lower-alkoxy, di-lower-alkylamino-lower-alkoxy and halogen; $R_9$ is selected from the group consisting of hydrogen, $CF_3$, lower-alkylamino-lower-alkoxy, di-lower-alkylamino-lower-alkoxy and halogen; and $R_{10}$ is selected from the group consisting of hydrogen, $CF_3$, lower-alkylamino-lower-alkoxy and di-lower-alkylamino-lower-alkoxy. Perferred compounds of general formula III are those reported in Table I as having an $IC_{50}$ of less than about 5 μM, more preferably less than about 1 μM.

Exemplary embodiments of the compounds of general formula III are described and the $IC_{50}$ values obtained therefor in W2 cells infected with a *Plasmodium falciparum* clone from CDC/Indochina III as hereinafter described are reported in Table I.

TABLE I

| # | Code | $R_1$ | $R_2$ | $R_3$ | $R_4$ | $R_5$ | $R_6$ | $R_7$ | $R_8$ | $R_9$ | $R_{10}$ | $IC_{50}$ (μM) |
|---|------|-------|-------|-------|-------|-------|-------|-------|-------|-------|----------|----------------|
|   | Chloroquine | | | | | | | | | | | 0.2 |
| 1 | RL388 | Cl | Cl | H | H | H | $CH_3O$ | H | $CH_3O$ | H | H | 0.38 |
| 2 | BG0410 | Cl | Cl | H | H | H | H | $CH_3O$ | $CH_3O$ | H | H | 0.39† |
| 3 | RL389 | Cl | H | Cl | H | H | $CH_3O$ | H | $CH_3O$ | H | H | 0.42 |
| 4 | RL391 | H | F | F | H | H | $CH_3O$ | H | $CH_3O$ | H | H | 0.47 |
| 5 | BG0101 | H | H | Cl | H | H | $CH_3O$ | H | $CH_3O$ | H | H | 0.63† |
| 6 | RL3128 | H | Cl | H | H | H | $CH_3O$ | H | $CH_3O$ | H | H | 0.74† |
| 7 | RL390 | F | H | F | H | H | $CH_3O$ | H | $CH_3O$ | H | H | 0.77 |
| 8 | RL3102 | H | Cl | H | Cl | H | Cl | H | Cl | H | H | 0.90 |
| 9 | RL387 | $CH_3O$ | H | H | H | H | $CH_3O$ | H | $CH_3O$ | H | H | 0.96 |
| 10 | RL3125 | F | H | H | F | H | $CH_3O$ | H | $CH_3O$ | H | H | 1.3† |
| 11 | RL3141 | H | H | $(CH_3)_2N$ | H | H | $CH_3O$ | H | $CH_3O$ | H | H | 1.4† |
| 12 | RL3100 | $CH_3O$ | H | $CH_3O$ | H | H | Cl | H | H | Cl | H | 1.9 |
| 13 | BG0417 | F | H | H | H | F | H | $CH_3O$ | $CH_3O$ | H | H | 2.0† |
| 14 | RL3126 | Cl | H | H | H | Cl | $CH_3O$ | H | $CH_3O$ | H | H | 2.4† |
| 15 | RL3123 | F | F | H | H | H | $CH_3O$ | H | $CH_3O$ | H | H | 2.8† |
| 16 | RL398 | $CH_3O$ | H | $CH_3O$ | H | H | H | Cl | Cl | H | H | 3.2 |
| 17 | RL334 | $CH_3O$ | H | $CH_3O$ | H | H | $CH_3O$ | H | $CH_3O$ | H | H | 3.6* |
| 18 | RL3105 | H | H | Cl | H | H | Cl | H | Cl | H | H | 3.6 |
| 19 | RLc04 | H | H | H | H | H | OH | OH | OH | H | H | 3.6 |
| 20 | RL397 | $CH_3O$ | H | $CH_3O$ | H | H | Cl | H | Cl | H | H | 3.8 |

TABLE I-continued

| # | Code | R₁ | R₂ | R₃ | R₄ | R₅ | R₆ | R₇ | R₈ | R₉ | R₁₀ | IC₅₀ (μM) |
|---|------|----|----|----|----|----|----|----|----|----|-----|-----------|
| 21 | RLc12 | OH | H | H | H | H | OH | H | OH | H | H | 3.9 |
| 22 | BG0407 | CH₃O | H | H | H | CH₃O | H | CH₃O | CH₃O | H | H | 4.2† |
| 23 | RL3127 | Cl | H | H | H | H | CH₃O | H | CH₃O | H | H | 5.8† |
| 24 | BG0402 | H | H | NO2 | H | H | H | CH₃O | CH₃O | H | H | 5.9† |
| 25 | RLc09 | CH₃O | H | H | H | H | OH | H | H | H | H | 6.9 |
| 26 | RLc13 | H | H | OH | H | H | OH | H | OH | H | H | 7.4 |
| 27 | BG0409 | Cl | H | H | H | Cl | H | CH₃O | CH₃O | H | H | 7.9† |
| 28 | RL3124 | F | H | H | H | F | CH₃O | H | CH₃O | H | H | 8.1† |
| 29 | BG0107 | CH₃O | H | H | H | CH₃O | CH₃O | H | CH₃O | H | H | 8.6† |
| 30 | BG0413 | H | Cl | H | Cl | H | H | CH₃O | CH₃O | H | H | 8.8† |
| 31 | RLc11 | H | H | H | H | H | OH | OH | OH | H | H | 10.1 |
| 32 | RL399 | CH₃O | H | CH₃O | H | H | F | H | F | H | H | 11.1 |
| 33 | RL3103 | Cl | H | Cl | H | H | H | Cl | Cl | H | H | 14.6 |
| 34 | RLc01 | OH | H | H | H | H | OH | H | H | H | H | 14.7 |
| 35 | BG0418 | H | F | F | H | H | H | CH₃O | CH₃O | H | H | 16.1† |
| 36 | RLc08 | H | CH₃O | CH₃O | H | H | OH | H | H | H | H | 16.4 |
| 37 | BG0401 | H | H | Cl | H | H | H | CH₃O | CH₃O | H | H | 16.6† |
| 38 | BG0408 | Cl | H | Cl | H | H | H | CH₃O | CH₃O | H | H | 19.5† |
| 39 | RLc03 | H | H | OH | H | H | OH | H | H | H | H | 23.0 |
| 40 | RL3104 | H | H | HCl | H | H | H | Cl | Cl | H | H | 31.7 |
| 41 | RLc02 | H | OH | H | H | H | OH | H | H | H | H | 77.0 |
| 42 | BG0415 | F | H | F | H | H | H | CH₃O | CH₃O | H | H | 109† |
| 43 | RL3101 | H | Cl | H | Cl | H | CH₃O | H | CH₃O | H | H | >148 |

*IC₅₀ of chloroquine 0.23 μM.
†IC₅₀ of chloroquine 0.2-0.4 μM.

In similar tests, compound 44 (RL3119)

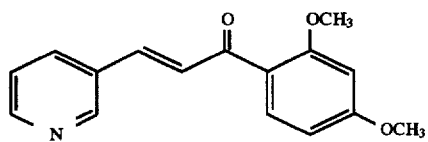

had an IC₅₀ of 3.1 μM (compared to an IC₅₀ of 0.2-0.4 μM for chloroquine).

Another preferred class of compounds having particular utility as inhibitors of metazoan parasite proteases have the general formula IV

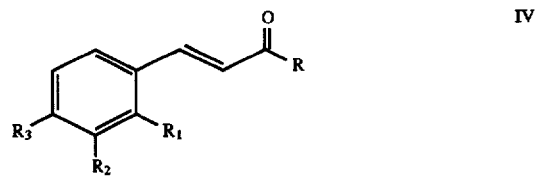

wherein each of $R_1$, $R_2$ and $R_3$ is independently selected from the group consisting of H, lower alkyl, lower alkoxy, nitro and halogen and R is selected from the group consisting of 2- and 3-pyridyl. Exemplary compounds of general formula IV are identified and IC₅₀ values therefor reported in Table II; also included therein is control compound cinnamoylimidazole 48 (RLc00), a commercially-available serine protease inhibitor, which has substantially no activity.

TABLE II

| # | Code | R₁ | R₂ | R₃ | R | IC₅₀ (μM) |
|---|------|----|----|----|---|-----------|
|   | Chloroquine |  |  |  |  | 0.2 |
| 44 | RL3119 |  |  |  |  | 3.1* |

TABLE II-continued

| # | Code | R₁ | R₂ | R₃ | R | IC₅₀ (μM) |
|---|------|----|----|----|---|-----------|
| 45 | RL3106 | CH₃O | H | CH₃O | 2-pyridyl | 4.6 |
| 46 | RL3107 | CH₃O | H | CH₃O | 3-pyridyl | 7.2 |
| 47 | RL3115 | H | NO₂ | Cl | 2-pyridyl | 8.2* |
| 48 | RLc00 (Cinnamoyl-imidazole) | H | H | H | imidazole | >253* |

Yet another class of compounds having particular utility as inhibitors for use in accordance with the present invention have the general formula V

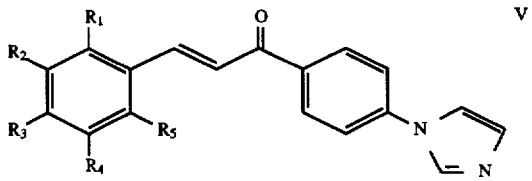

wherein each of $R_1$–$R_5$ is independently selected from the group consisting of H, halogen, lower alkyl, lower alkoxy, lower-alkylamino and di-lower-alkylamino. Exemplary compounds of general formula V are identified and IC₅₀ values therefor reported in Table III.

TABLE III

| # | Code | $R_1$ | $R_2$ | $R_3$ | $R_4$ | $R_5$ | $IC_{50}$ (μM) |
|---|------|-------|-------|-------|-------|-------|----------------|
|   | Chloroquine | | | | | | 0.2–0.4 |
| 49 | RL3136 | Cl | H | Cl | H | H | 0.72 |
| 50 | RL3138 | H | Cl | H | Cl | H | 0.91 |
| 51 | RL3135 | Cl | Cl | H | H | H | 1.8 |
| 52 | RL3137 | Cl | H | H | H | Cl | 1.9 |
| 53 | RL3130 | F | H | F | H | H | 3.2 |
| 54 | RL3132 | F | H | H | H | F | 7.8 |
| 55 | RL3124 | H | H | $(CH_3)_2N$ | H | H | 18 |

In similar tests, compound 56 (RL3111)

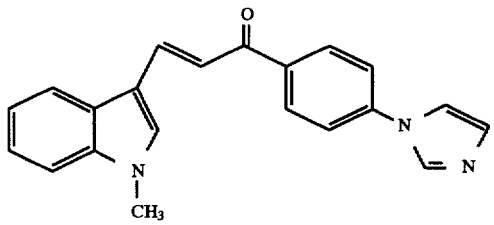

had an $IC_{50}$ of 20 μM (compared to an $IC_{50}$ of 0.2–0.4 μM for chloroquine).

Yet another class of compounds having particular utility as inhibitors for use in accordance with the present invention have the general formula VI

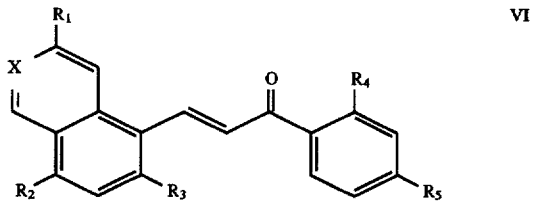

VI wherein X is N or $CR_6$ in which $R_6$ is H or lower alkyl, each of $R_1$–$R_3$ is independently selected from the group consisting of H, halogen, lower alkyl, lower alkoxy, lower-alkylamino and di-lower-alkylamino, and each of $R_4$ and $R_5$ is independently selected from the group consisting of hydroxyl and lower-alkoxy. Exemplary compounds of general formula V are identified and $IC_{50}$ values therefor reported in Table IV.

TABLE IV

| # | Code | X | $R_1$ | $R_2$ | $R_3$ | $R_4$ | $R_5$ | WR, $IC_{50}$ (μM) |
|---|------|---|-------|-------|-------|-------|-------|--------------------|
|   | Chloroquine | | | | | | | 0.23 |
| 57 | RL372 | N | Cl | $CH_3O$ | $CH_3O$ | $CH_3O$ | $CH_3O$ | 2.0 |
| 58 | RL370 | N | Cl | $C_2H_5O$ | $C_2H_5O$ | $CH_3O$ | $CH_3O$ | 2.9 |
| 59 | RL342 | C | H | H | $CH_3O$ | $CH_3O$ | $CH_3O$ | 9.7 |
| 60 | RL365 | C | H | H | $CH_3O$ | OH | $CH_3O$ | >150 |

Of the compounds tested, 11 compounds had $IC_{50}$ values at submicromolar levels. The best compound tested, compound 1 (RL388), had an $IC_{50}$ value of 0.38 μM.

Some trends with respect to the structure-activity relationship in the compounds of the present invention were noted. Substitution with halogen (e.g., F or Cl) on the A ring and with lower-alkoxy (e.g., methoxy) on the B ring generally increased activity; this is illustrated by compounds 1–8, with $IC_{50}$ values at submicromolar levels. The best embodiments tested thus far include compounds in which $R_1$ and $R_2$ are Cl (the corresponding F-substituted compound 15 had an $IC_{50}$ of 2.8 μM) and $R_6$ and $R_8$ (compound 1) or $R_7$ and $R_8$ (compound 2) are lower-alkoxy (e.g., methoxy). There were, however, a number of exceptions (see, e.g., compounds 23, 27, 28, 30, 35, 37, 38, 42 and 43).

Some of the compounds tested had limited solubility, even in dimethylsulfoxide; this would be expected to reduce the activity observed. To compensate therefor, it is presently preferred in some embodiments that ring B comprise one or more lower-alkylamino-lower-alkoxy or di-lower-alkylamino-lower-alkoxy (e.g., dimethylaminoethyloxy) groups. Salts of such compounds would typically have increased water solubility.

Electron-withdrawing groups on the A ring and electron-donating groups on the B ring appeared to increase overall antimalarial activity. Again, some exceptions were noted; for example, compounds 9, 11 and 12 (which have electron-donating groups on the A ring) had $IC_{50}$ values of 1 to 2 μM, although at pH 5 or below the dimethylamino group of compound 11 would likely be positively-charged and therefore act as a strong electron-withdrawing group. In addition, compound 24 with a strong electron-withdrawing nitro group at $R_3$ had poor activity. Compounds wherein the A ring is perhalogenated (e.g., A is pentafluoro- or pentachlorophenyl) or either or both rings comprise at least one $CF_3$ group are of particular interest.

Compounds with hydroxyl groups on both rings (e.g., compound 21) have activity similar to that of hydrazide derivative IV44A disclosed in the aforementioned PCT published application WO 94/06280. They are expected, however, to be more water soluble.

In general, the three-fingered compounds 49–56 with imidazole as the third ring have similar patterns of preference for electron-withdrawing and electron-donating groups as described above for the two-fingered compounds.

Many of the inhibitors employed in accordance with the present invention are either known compounds (some of which are commercially available) or may be readily prepared in a manner known per se from heretofore known and/or commercially-available compounds. The following general schemes illustrate some particularly advantageous synthetic routes; alternative syntheses will of course be readily apparent to those skilled in the field of synthetic organic chemistry.

The compounds of general formula I are known per se and/or may be prepared in an essentially routine manner from heretofore known compounds. While those working in the field would immediately appreciate that other routes for preparation thereof are available, one set of particularly advantageous synthetic schemes for the compounds of general formulas III–VI are as depicted below.

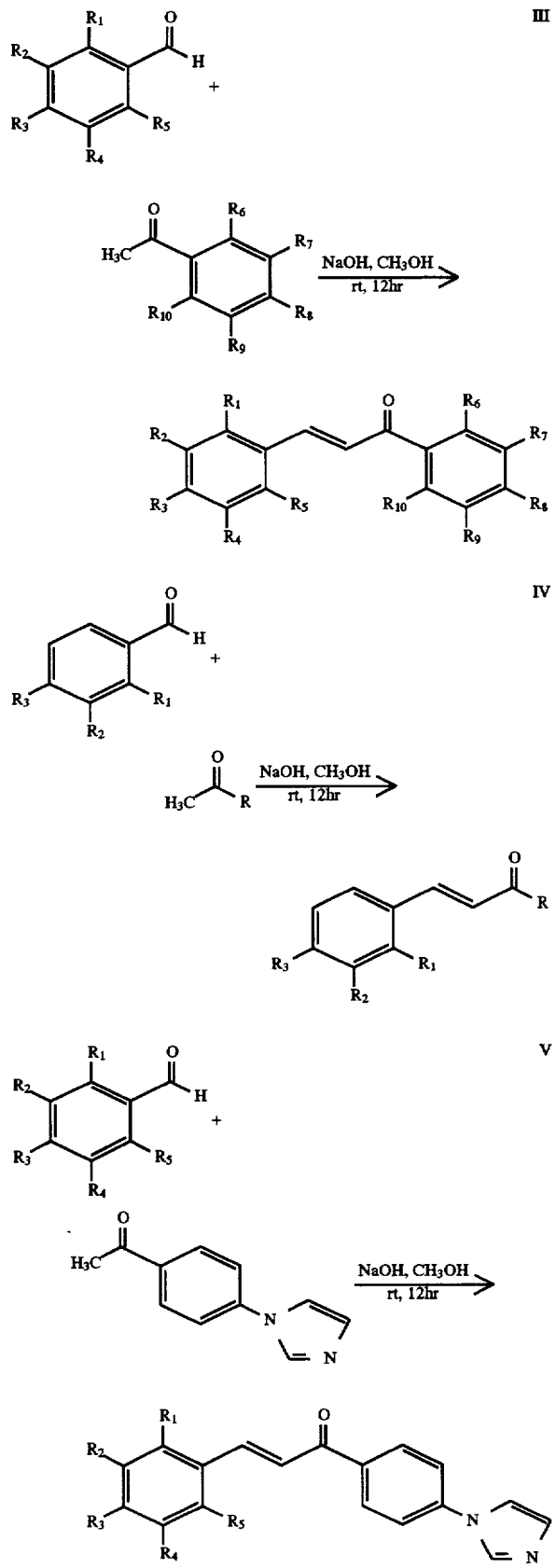

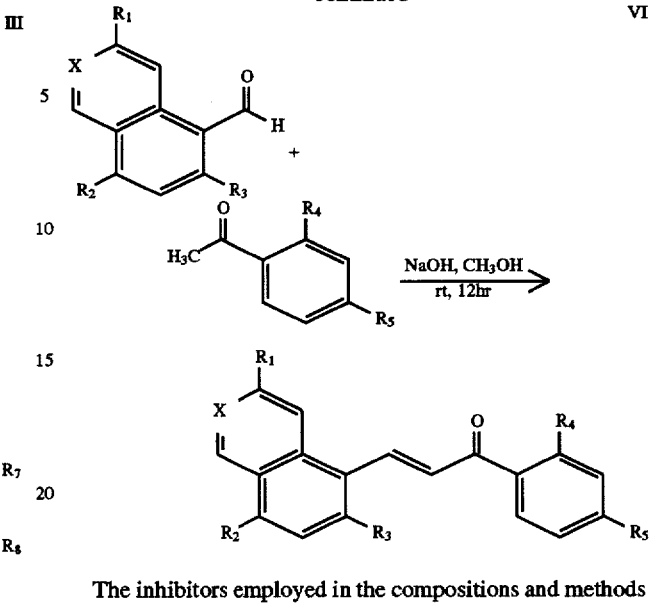

The inhibitors employed in the compositions and methods of the present invention are typically administered in conjunction with a suitable carrier or adjuvant. It is presently preferred that the inhibitors be administered in an aqueous solution (e.g., buffered saline); however, other suitable excipients and adjuvants would be readily apparent to those of skill in the art. The compositions of the invention may be administered by a wide variety of known routes of administration (e.g., orally, intravenously, subcutaneously, etc.). The inhibitors are suitably administered at a dosage of about 0.01 to about 10 µM, and preferably about 0.01 to about 1 µM, per kilogram of body weight of the patient per day. Of course, as would be appreciated by those of skill in the art, the optimum dosage for treatment of any given parasitic infection with a composition of the present invention comprising one or more specific inhibitors as described herein may readily be determined empirically.

The inhibitors determined to be effective in accordance with the present invention exhibit a surprising specificity for the malarial protease and other evolutionarily-related metazoan parasite proteases. These metazoan parasite proteases are distinct from proteases found in the parasitic hosts (i.e., mammals), particularly with respect to the chemical environments of the active sites of the respective enzymes. In view of the significant differences between corresponding subsites in the mammalian and the metazoan parasite proteases, the inhibitors of the present invention do not in general inhibit the activity of the host's essential proteases (e.g., cathepsin B).

For example, the malarial enzyme has an asparagine at position 133, a key residue for determining the specificity of bonding at the S2 subsite; for most other non-parasitic cysteine proteases, however, this residue tends to be either branched hydrophobic or alanine. Specific interactions of the inhibitors in accordance with the present invention with the asparagine increase both specificity and potency. Another modulating residue is glutamic acid at position 205 in the malarial enzyme. The side chain rotamer located at the base of the S2 binding pocket is postulated to change depending upon the nature of the interaction at S2. If the substituent is hydrophobic, the glutamic acid points away from the S2 pocket and presumably interacts with solvent; however, when the substituent is basic, the glutamic acid is thought to point towards the S2 pocket and provide a crucial interaction with the positive charge. Inhibitors that exploit this interaction (i.e., those wherein ring system A has some basic characteristics as a part of the ring system and/or by virtue of the substitution pattern) are thus of particular interest.

The invention may be better understood with reference to the accompanying example, which is intended for purposes of illustration only and should not be construed as in any sense limiting the scope of the present invention as defined in the claims appended hereto.

EXAMPLE

The Walter Reed Army Institute of Research (WRAIR) in vitro screens for intrinsic antimalarial activity are based on modifications of procedures described in the literature [Desjardins, R. E. et al. (1979)J. D. Antimicrobial Agents and Chemotherapy, 16(6):710–8]; Chulay et al. (1983) [Journal of Infectious Diseases 148(1):148–55]; Milhous, W. K. et al.(1985)[Antimicrobial Agents and Chemotherapy 27(4):525–30]. The system is directed to the assessment of the intrinsic activity against the erythrocytic asexual life cycle (blood schizontocides)]. A minimum of 10 mg of sample is generally submitted for initial testing. Two Plasmodium falciparum clones from CDC/Indochina III (W-2) and CDC/Sierra Leone I (D-6) [Oduola, A. M. et al. (1988) [Experimental Parasitology 67(2):354–60] are used for all assays. W-2 is resistant to chloroquine, quinine and pyrimethamine and susceptible to mefloquine. D-6 is resistant to mefloquine and susceptible to chloroquine, quinine and pyrimethamine.

The clones are maintained in continuous log-phase growth in RPMI-1640 medium supplemented with 6% washed human A+ erythrocytes, 25 mM Hepes, 32 nM $NaHCO_3$ and 10% heat inactivated A+ human plasma or albuMAX™ (lipid-rich bovine serum albumin, GIBCO, Grand Island, N.Y.). All cultures and assays are conducted at 37° C. under an atmosphere of 5% $CO_2$ and 5% $O_2$, with a balance of $N_2$.

The preliminary screen uses D-6 diluted to a 0.2% parasitemia in a 1% hematocrit in folic acid free and p-aminobenzoic acid free RPMI-1640 and albuMAX™ (FF-CM). Typically, five mg of the compound are dissolved in 250 µl of dimethyl sulfoxide (DMSO). The compound is further diluted to a stock solution to 10 ml with FF-CM. This stock solution is kept at −70° C. until used. The clone is preexposed, in duplicate, at three concentrations (50,000 ng/ml, 5,000 ng/ml and 50 ng/ml) of the test compound for 48 hr in a 96-well microtiter plate (MTP) using a Biomek® 1000 automated laboratory workstation (Beckman Instruments, Fullerton, Calif.). Each MTP contains chloroquine-containing controls to assess the relative activity of the unknown compound and to monitor the response of D-6.

After the preincubation, [³H]-hypoxanthine is added to each well of the MTP to determine if the parasites can still replicate or repair DNA. After 66 hr of total incubation time, the MTP are frozen to lyse the erythrocytes and parasites. The parasite DNA is recovered by harvesting the lysate onto glass-fiber filters using a Mark II cell-harvester (Tomtec, Orange, Conn.). The radioactivity is counted on a 1205 Betaplate™ liquid scintillation counter (Wallac, Turku, Finland). The results are recorded as counts per minute (CPM) per well at each drug concentration divided by the arithmetic mean of the CPM from the three untreated infection parasite controls wells.

If the compound does not affect parasite growth at 50,000 ng/ml, it is classified as inactive. If the compound suppresses greater than two standard deviations from the arithmetic mean of the untreated infection controls at 50,000 ng/ml, but less than 50% at 5,000 ng/ml, the compound is designated as partially active. However, if the compound suppresses greater than 50 percent of the incorporation of [³H] hypoxanthine relative to untreated infection control parasites at 5,000 ng/ml, the compound is classified as active and is further evaluated by a two-fold serial dilutions to determine the $IC_{50}$ values (50% inhibitory concentration) for each compound.

The serial dilution assay is conducted using the same assay conditions and stock solution of the compound used for the preliminary screen. Both the D-6 and the W-2 clones are used. The compound is diluted two-fold over 11 different concentration ranges with a starting concentration that is based on the preliminary screen. The $IC_{50}$ is determined by a non-linear logistic dose response analysis (TableCurve™, Jandel Scientific, Corte Madera, Calif.). If the results from the assay do not agree with the concentration ranges of the preliminary screen, the assay is repeated. For each assay, the $IC_{50}$ for each clone is determined against the known antimalarials chloroquine, mefloquine, artemisinin, quinine and pyrimethamine. These control values establish the unknown compound's relative parasite susceptibility profile compared to known antimalarials. $IC_{50}$s can be similarly determined for drug-resistant isolates/clones from a wide variety of geographic locations.

From the foregoing description, one skilled in the art can readily ascertain the essential characteristics of the invention and, without departing from the spirit and scope thereof, can adapt the invention to various usages and conditions. Changes in form and substitution of equivalents are contemplated as circumstances may suggest or render expedient, and any specific terms employed herein are intended in a descriptive sense and not for purposes of limitation.

What is claimed is:

1. A method for treating a patient infected with a metazoan parasite, said method comprising administering an amount effective to kill the parasite of at least one metazoan protease inhibitor of general formula

A—X—B wherein A is a substituted or unsubstituted homoaromatic ring system comprising one to three rings which binds to at least one of the S2, S1 and S1' subsites;

B is a substituted or unsubstituted homoaromatic ring system comprising one to three rings which binds to at least one of the S1', S1 and S2 subsites; and X is —C=C—C(=O)—.

2. A method according to claim 1, wherein the metazoan parasite is selected from the group consisting of Plasmodium falciparum, Schistosoma mansoni, Trypanosoma cruzi, Giardia lamblia, Entoemeba histolytica, Cryptospiridium spp., Leishmania spp., Brugia spp., Wuchereria spp., Onchocerca spp., Strongyloides spp., Coccidia, Haemanchus spp., Ostertagia spp., Trichomonas spp., Dirofilaria spp., Toxocara spp., Naegleria spp., Pneumocystis carinii, Ascaris spp., other Trypanosoma spp., other Schistosome spp., other Plasmodium spp., Babesia spp., Theileria spp., Anisakis and Isospora bell.

3. A method according to claim 1, wherein the metazoan protease inhibitor is administered at a dosage of about 0.01 to about 10 µM per kilogram of body weight of patient per day.

4. A method according to claim 3, wherein the metazoan protease inhibitor is administered at a dosage of about 0.01 to about 1 µM per kilogram of body weight of patient per day.

5. A method according to claim 1, wherein at least one of A and B is substituted by at least one substituent selected from the group consisting of hydroxyl, lower alkyl, lower alkoxy, amino, mono- and di-(lower-alkyl)-amino, —$NO_2$, halogen, aryl, aryloxy, —COOH and —COOR', wherein R' is lower alkyl or aryl.

6. A composition for treating a patient infected with a metazoan parasite, said composition comprising a suitable carrier or excipient and an amount effective to kill the parasite of at least one metazoan protease inhibitor of general formula

A—X—B wherein A is a substituted or unsubstituted homoaromatic ring system comprising one to three rings which binds to at least one of the S2, S1 and S1' subsites;

B is a substituted or unsubstituted homoaromatic ring system comprising one to three rings which binds to at least one of the S1', S1 and S2 subsites; and X is —C=C—C(=O)—.

7. A composition according to claim 6, in a dosage unit form wherein the metazoan protease inhibitor is present in an amount sufficient to provide about 0.01 to about 10 µM per kilogram of body weight of patient per day.

8. A composition according to claim 7, in a dosage unit form wherein the metazoan protease inhibitor is present in an amount sufficient to provide about 0.01 to about 1 µM per kilogram of body weight of patient per day.

9. A composition according to claim 6, wherein at least one of A and B is substituted by at least one substituent selected from the group consisting of hydroxyl, lower alkyl, lower alkoxy, amino, mono- and di-(lower-alkyl)-amino, —$NO_2$, halogen, aryl, aryloxy, —COOH and —COOR', wherein R' is lower alkyl or aryl.

* * * * *